United States Patent

Sugawara et al.

[11] Patent Number: 5,550,380
[45] Date of Patent: Aug. 27, 1996

[54] RADIATION IMAGE DETECTING APPARATUS INCLUDING BUNDLED OPTICAL FIBERS

[75] Inventors: Takeo Sugawara; Toshihiko Hino; Makoto Suzuki, all of Hamamatsu, Japan

[73] Assignee: Hamamatsu Phontonics K.K., Hamamatsu, Japan

[21] Appl. No.: 376,280

[22] Filed: Jan. 20, 1995

[30] Foreign Application Priority Data

Jan. 21, 1994 [JP] Japan .................................. 6-005438

[51] Int. Cl.⁶ .................................. A61B 6/14; G01T 1/20
[52] U.S. Cl. ............... 250/370.11; 250/368; 250/370.09; 378/38
[58] Field of Search .................................. 378/38, 39, 40; 250/368, 370.09, 370.11; 385/116, 120

[56] References Cited

U.S. PATENT DOCUMENTS

| | | | |
|---|---|---|---|
| 3,402,000 | 9/1968 | Crawford | 385/116 |
| 4,057,733 | 11/1977 | Hofmockel et al. | 378/38 |
| 4,878,234 | 10/1989 | Pfeiffer et al. | 250/370.09 |
| 4,910,405 | 3/1990 | Suzuki et al. | 250/368 |
| 5,074,683 | 12/1991 | Tam et al. | 385/120 |
| 5,079,423 | 1/1992 | Hagiwara et al. | 250/368 |
| 5,138,166 | 8/1992 | Makino et al. | 250/368 |

FOREIGN PATENT DOCUMENTS

| | | |
|---|---|---|
| 0373717 | 6/1990 | European Pat. Off. . |
| 0372122 | 6/1990 | European Pat. Off. . |
| 63-311193 | 12/1988 | Japan . |
| 1-227583 | 9/1989 | Japan . |
| 2-249537 | 10/1990 | Japan . |
| 2-276996 | 11/1990 | Japan . |

*Primary Examiner*—Carolyn E. Fields
*Attorney, Agent, or Firm*—Cushman Darby & Cushman, L.L.P.

[57] ABSTRACT

An apparatus comprises a fiber optic device having a plurality of cores buried in a cladding, a first luminescent screen fixed to an input face of said fiber optic device, and a first CCD image sensor fixed to an output face of the fiber optic device. The CCD image sensor comprises a package, a CCD chip fixed in the package, lead pins penetrating said package, and bonding wires connecting said lead pins to said CCD chip. The CCD chip comprises an image pickup region for converting a ray incident thereto into an electric signal, and bonding pads in contact with said bonding wires and wherein said output face is in contact with said image pickup region and said output face is not in contact with said bonding pads.

17 Claims, 10 Drawing Sheets

RADIATION IMAGE DETECTING APPARATUS INCLUDING BUNDLED OPTICAL FIBERS

BACKGROUND OF THE INVENTION

1. Field of the Invention

The present invention relates to a radiation image detecting apparatus used in the fields of industry, medicine, etc.

2. Related Background Art

The conventional radiation detecting apparatus are described for example in Japanese Laid-open Patent Applications No. 63-311193, No. 1-227583, No. 2-276996, and No. 2-249537, U.S. Pat. Nos. 4,910,405, 5,079,423, and 5,138,166, and European Patent Publication No. 0373717 A1.

SUMMARY OF THE INVENTION

The apparatus according to the present invention is an improvement in the conventional apparatus and can detect a ray image with higher accuracy than the conventional apparatus. The present inventors found difficulty in reaching the present invention. It was because the conventional apparatus employed a glass cover on a package in order to prevent dust from attaching to a CCD chip and this glass cover seemed essential.

The apparatus of the invention can obtain a sharp image by direct contact of a fiber optic device with the CCD chip. To avoid dust from attaching to the CCD chip, the CCD package is sealed by the fiber optic device. A device was necessary for the sealing structure.

The detecting apparatus of the invention is provided with a first module. This first module comprises a first fiber optic device, a first luminescent screen, and a first CCD image sensor.

The fiber optic device comprises a plurality of optical fibers fixed to each other. Since the optical fibers are fixed to each other, the fiber optic device is free of deformation. The optical fibers each have a cladding and a core buried in the cladding. A refractive index of the core is higher than that of the cladding. The core and cladding are made of glass. This fiber optic device is formed by burying a plurality of cores in a single cladding.

The fiber optic device has an input face which light enters and an output face which light leaves. The input face and output face include end faces of the optical fibers. A ray of light entering the input face propagates in an optical fiber to leave the output face.

A luminescent screen (luminescent film) is fixed to the input face. The luminescent screen converts a radioactive ray incident thereinto into a luminescent ray. The luminescent ray appearing in the luminescent screen propagates in an optical fiber to emerge from the output face of the fiber optic device.

The CCD image sensor is fixed to the output face. The CCD image sensor comprises a package and a CCD chip attached to the package. The package has a recessed portion. The fiber optic device has a projected portion. The projected portion of the fiber optic device includes the output face. The projected portion of the fiber optic device fits in with the recessed portion of the package of the CCD image sensor. Accordingly, the fiber optic device is stuck to the CCD image sensor, whereby they are stationary to each other.

The CCD chip has a main surface. The main surface has an image pickup region comprised of a plurality of pixels, and an output region in which bonding pads for collecting signals from the pixels are formed. The image pickup region is a surface to which the luminescence generated in the luminescent screen is incident. The image pickup region of the CCD chip is opposed to the output face of the fiber optic device.

An angle of a normal line to the output face with an optical axis of each core in the fiber optic device is 45 degrees. The image pickup region of the CCD chip is parallel to the output face of the fiber optic device. An angle between the optical axis of each core and a normal line to the input face is 45 degrees. The luminescent screen (luminescent surface) is parallel to the input face.

The output face includes the end faces of the plurality of cores. The input face includes the end faces of the plurality of cores. A density of the end faces of the plurality of cores in the output face is equal to that of the end faces of the cores in the input face. Each core extends straight. The optical axis of each core is a straight line. Accordingly, a ray image into the input face of the fiber optic device is outgoing at 1:1 magnification from the output face. Further, there is no distortion caused in the image.

The image pickup region of the CCD chip is in contact with the output face of the fiber optic device. Therefore, the image entering the image pickup region is not disturbed by any intervening members between the image pickup region and the output face, thus forming a clear image on the image pickup region.

In the detecting apparatus of the present invention, the image pickup region of the CCD chip is in direct contact with the output face of the fiber optic device in order to obtain a clear image. The output region of the CCD chip where the bonding pads are formed restricts this "direct contact." The output region is separate from the output face. Since the output face is not in direct contact with the output region, the bonding pads, and bonding wires connecting between the bonding pads and lead pins are prevented from being damaged by the fiber optic device. Thus, the bonding wires stand long use.

The CCD chip comprises a semiconductor substrate, an insulating film on and in contact with the semiconductor substrate, transfer electrodes in contact with the insulating film, a protective film formed over the transfer electrodes, a first signal line for applying a predetermined drive voltage to the transfer electrodes, a first bonding pad connected to the first signal line on the semiconductor substrate, a floating diffusion amplifier for collecting signals (charge) transferred from the transfer electrodes, and a second bonding pad connected to the floating diffusion amplifier. The output region is a region where the first and second bonding pads are formed.

The detecting apparatus of the present invention is provided with a second module. The second module has the same structure as the first module, having a second fiber optic device, a second luminescent screen, and a second CCD image sensor. The second luminescent screen is formed on a same plane as the first luminescent screen is. A normal line to the first luminescent screen (luminescent surface) is parallel to a normal line to the second luminescent screen. Thus, the normal line to the first luminescent screen (luminescent surface) and the normal line to the second luminescent screen are substantially parallel to each other. An angle between these normal lines is smaller than 5 degrees.

The first module and second module are set in a housing. The housing has a radiation shielding member. The radiation shielding member is made of lead. The housing has a barrel portion. The barrel portion has an opening. A radiation to be detected goes through the opening into the luminescent screen. The barrel portion is made of lead. Lead does not transmit radiations. Since this detecting apparatus has the barrel portion, directivity of incident radiations can be enhanced. The barrel portion has an opening edge, an inner surface intersecting with the opening edge, and an outer surface intersecting with the opening edge. The barrel portion interrupts radiations obliquely incident relative to the axis of the barrel portion of the detecting apparatus from the outside thereof.

The first CCD image sensor in the first module is fixed to a first circuit board for processing signals output from the CCD image sensor. The second image sensor is fixed to a second circuit board for processing signals output from the CCD image sensor. The first circuit board comprises a first print board. The second circuit board comprises a second print board. The first print board is opposed to the second print board. The first print board is nearly parallel to the second print board. An angle between normal lines to the first print board and to the second print board is less than 5 degrees. The first print board and second print board are fixed to the housing.

The detecting apparatus has a radiation source connected to the housing. A hollow connecting member connects the housing with the radiation source. Wiring for supplying drive power to the radiation source passes through inside the connecting member. Rubber is wound around the connecting member. When teeth are in contact with the rubber, the radiation source is held by the teeth.

This detecting apparatus comprises a display for displaying the signals output from the CCD image sensor. The display and CCD image sensor are electrically connected to each other through a display controller. The display controller controls the display to indicate the signals output from the CCD image sensor on the display.

The present invention decreases a temporal difference between entrance of a ray into the scintillator and arrival thereof at the solid state image sensing device. A radiation detector of the present invention is smaller than those in the conventional apparatus.

Since the scintillator generating visible rays with reception of radiations is perpendicular to a ray input face of the solid state image sensing device, the length of the optical fiber plate can be shortened in the direction of ray incidence and radiations through the scintillator are prevented from directly entering the ray input face of the solid state image sensing device.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 9:
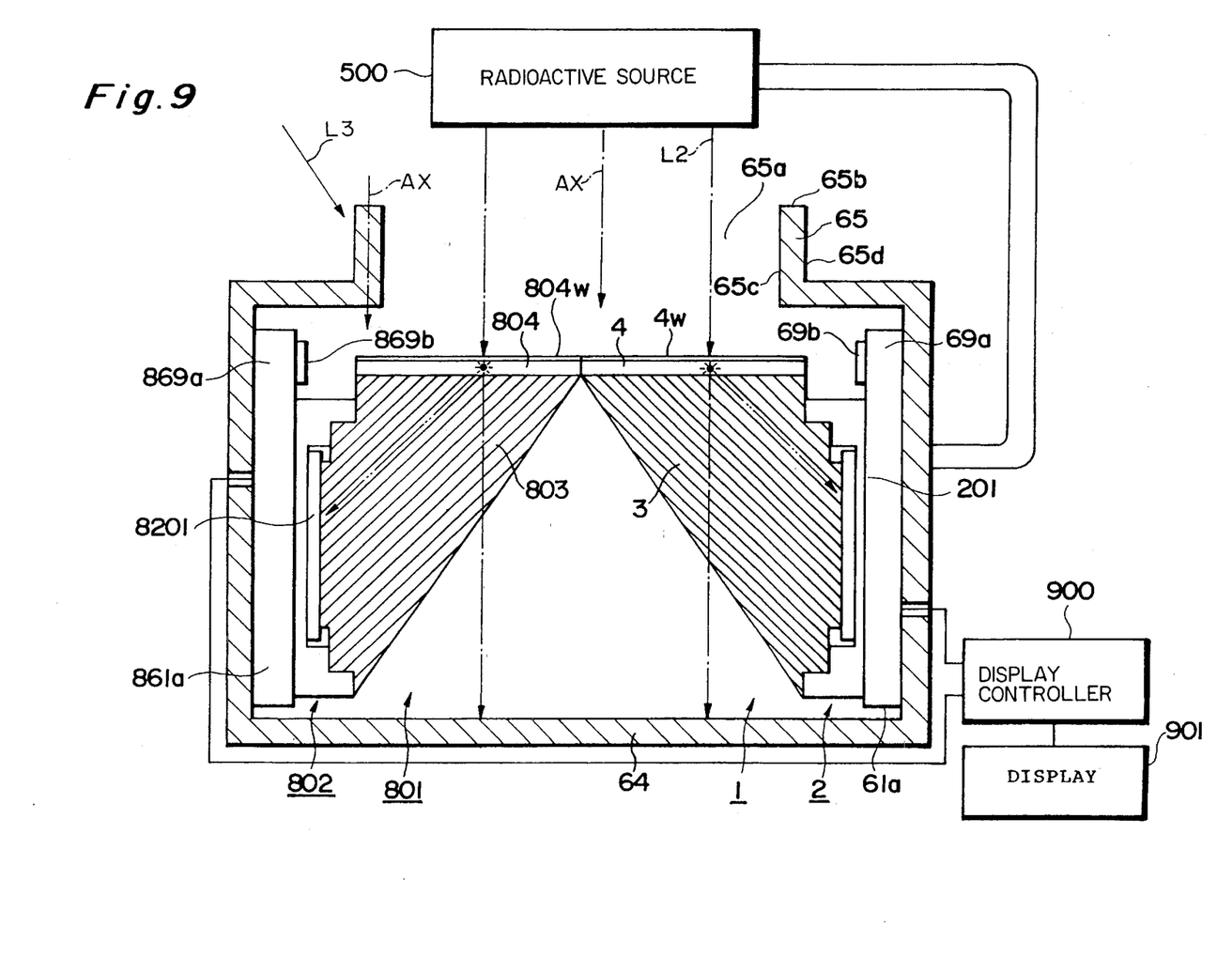
FIG. 9 is a drawing to show a detecting apparatus of an embodiment.

FIG. 9 shows an apparatus AP for detecting radiations. This apparatus AP is provided with an apparatus 1 for detecting radiations.

Figure 1:
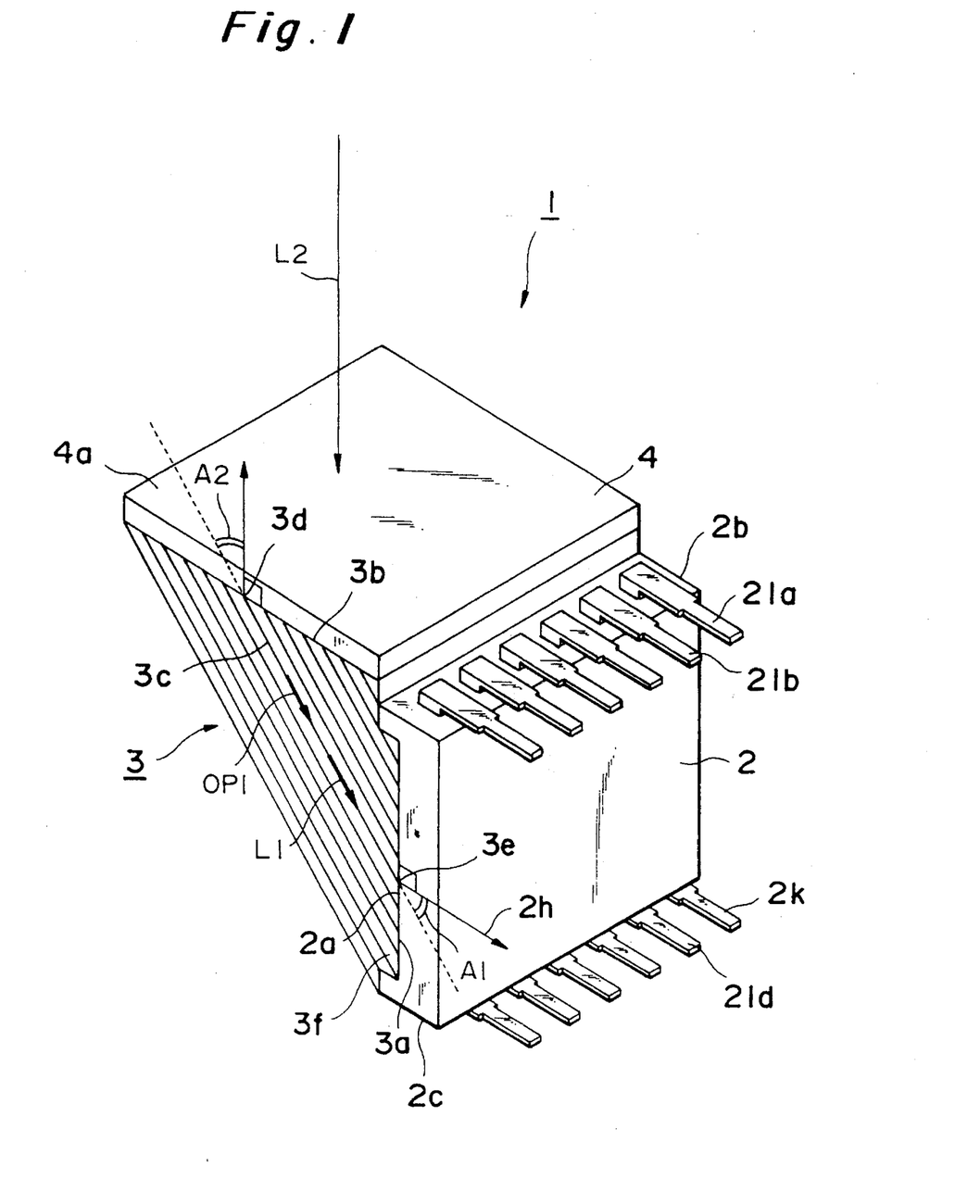
FIG. 1 is a perspective view to show a radiation image detector of an embodiment.

FIG. 1 shows the apparatus 1 for detecting radiation.

As shown, the radiation image detector 1 is provided with an optical fiber plate 3 having a ray output face 3a and a ray input face 3b each intersecting at an angle of 45° with a direction of waveguide of light L1 and nearly perpendicular to each other, a scintillator 4 fixed to the ray input face 3b and emitting light depending upon radiation L2 incident thereinto, and a CCD 2 as a solid state image sensing device a ray entrance surface 2a of which is provided on the ray output face 3a.

The ray entrance surface 2a of CCD 2 (the ray output face 3a of fiber plate 3) is nearly perpendicular to the input face 3b where the light L1 enters the optical fiber plate 3. There are a plurality of terminals 21a–21d provided on both side faces 2b, 2c of CCD 2.

The optical fiber plate 1 is produced as follows. First, a plurality of optical fibers are prepared. Then these optical fibers are bundled. Next, the bundle of these optical fibers are drawn while heated and stacked. This step is repeated several times. These optical fibers are pressed in hot temperature. Then a resultant product formed by these steps is cooled. Subsequently, the hardened bundle of optical fibers is cut into the shape shown in FIG. 1.

In the optical fiber plate shown in FIG. 1, the light L1 propagates in the direction of the optical axis OP1 of core 3c.

A ray input port 3d of core 3c is in the ray input face 3b of optical fiber plate 3. A ray output port 3e of core 3c is in the ray output face 3a of optical fiber plate 3.

Thus, the light L1 entering the fiber plate 3 at the ray input face 3b of optical fiber plate 1 is outgoing from the ray output face 3a.

Figure 2A:
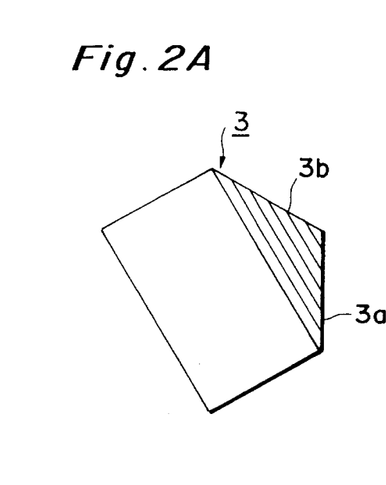
FIG. 2A to FIG. 2F are perspective views to show optical fiber plates used in the radiation image detector of the embodiment.
Figure 2B:
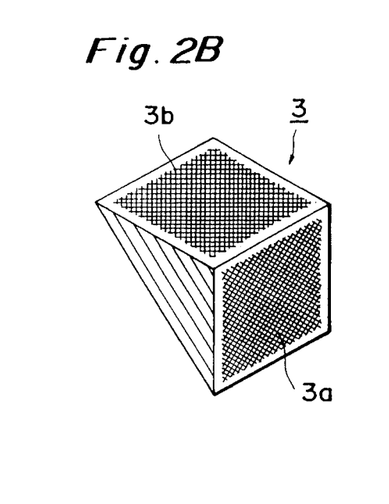
Figure 2C:
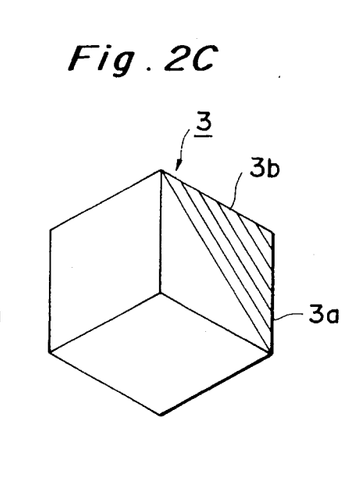
Figure 2D:
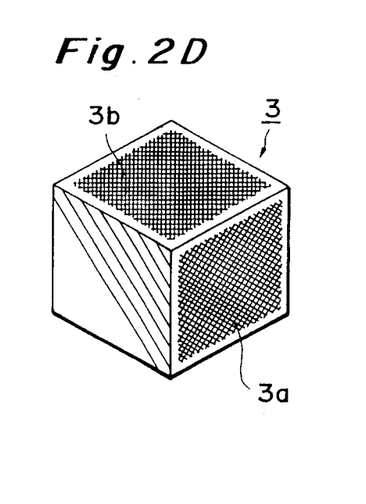
Figure 2E:
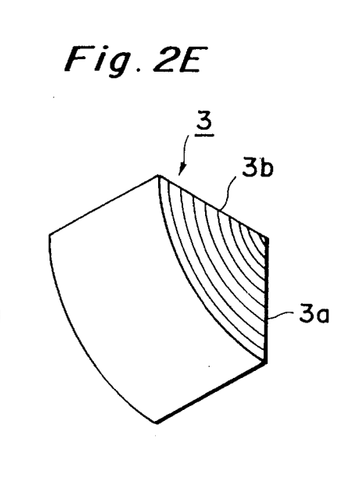
Figure 2F:
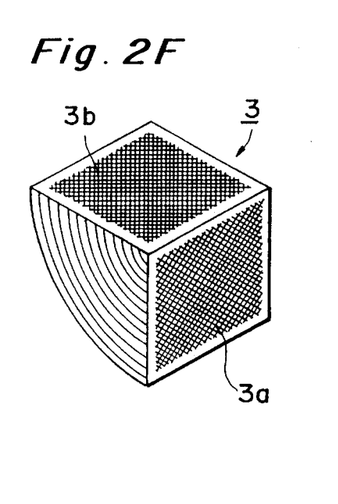

The shape of optical fiber plate 3 may be a triangular prism with a right triangle as the base as shown in FIG. 2A and FIG. 2B, a rectangular prism as shown in FIG. 2C and FIG. 2D, or a cylindrical member with a sector as the base as shown in FIG. 2E and FIG. 2F. The ray output face 3A and ray input face 3B are substantially perpendicular to each other in each of the fiber plates 3 shown in FIG. 2A to FIG. 2F.

The optical fiber plate 3 has a projected portion 3f. The projected portion 3f of the fiber plate 3 is fit in a recessed portion of CCD 2, and the fiber plate 3 is fixed to CCD 2.

The present apparatus is provided with the optical fiber plate 3 having the ray output face 3a and the ray input face 3b each intersecting with the direction of waveguide OP1 of the light L1 and nearly perpendicular to each other, the CCD 2 provided on the ray output face 3a, and the scintillator provided on the ray input face 3b. When a radiation L2 enters the scintillator 4, a ray L1 is produced in the scintillator 4 to propagate in the direction of waveguide OP1 of light L1. The ray L1 outgoing from the ray output face 3a enters the ray entrance surface 2a of CCD 2.

The ray L1 emitted in the scintillator 4 propagates in the waveguide direction OP1 of light L1 to enter the ray entrance surface 2a of CCD 2 nearly perpendicular to the surface 4a of scintillator 4 where the radiation L2 is incident. Since the ray entrance surface 2a of CCD 2 is nearly perpendicular to the surface 4a of scintillator 4 where the radiation L2 enters the scintillator 4, the radiation L2 incident nearly normal to the entrance surface 4a of scintillator 4 travels straight as nearly perpendicular to the normal line 2n to the ray entrance surface 2a of CCD 2. Accordingly, no radiation L2 is incident into the ray entrance surface 2a of CCD 2. Further, no radiation L2 is guided into CCD 2 by the optical fiber plate 3 optically coupling the ray entrance surface 2a of CCD 2 with the scintillator 4.

Even if the radiation L2 is transmitted by the optical fiber plate 3 without being absorbed thereby, the radiation does not directly enter the ray entrance surface 2a of CCD 2.

Since no radiation L2 directly enters the CCD the CCD 2 is prevented from being damaged by incidence of the radiation L2 thereinto. Noise due to the radiation L2 is reduced because the radiation L2 does not enter the CCD 2.

The radiation L2 includes X-rays. The radiation L2 is an electromagnetic wave generating light when entering the scintillator 4. The radiation L2 is not refracted so much in the optical fiber plate 3. The radiation L2 may be γ-rays.

Figure 3A:
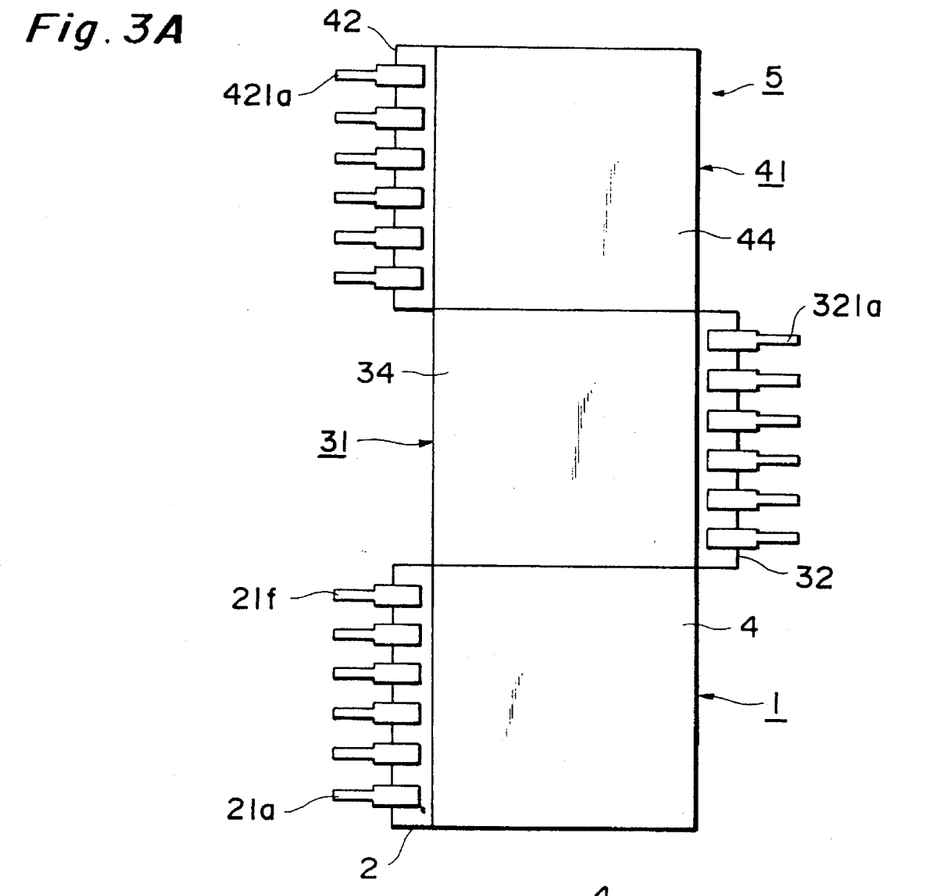
FIG. 3A is a plan view to show a radiation image detecting module of an embodiment.
Figure 3B:
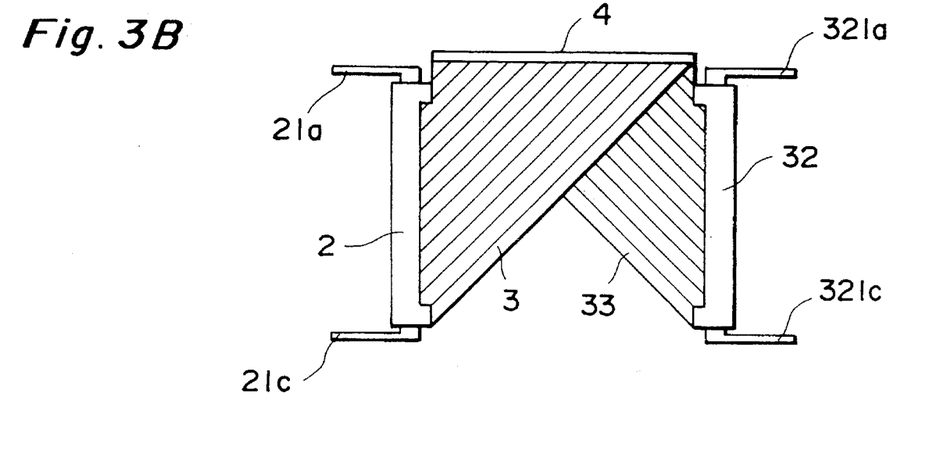
FIG. 3B is a front elevation to show the radiation image detecting module of the embodiment.

FIG. 3A is a plan view of an apparatus 5 for detecting radiations. FIG. 3B is a front elevation of the apparatus 5.

As shown in FIGS. 3A and 3B, this radiation image detecting module 5 is provided with the radiation detector 1. This apparatus 5 is further provided with a detector 31 and a detector 41. The detector 31 and detector 41 are the same as the detector 1. Scintillators (luminescent screens) 4, 34, 44 are arranged on a same plane. The scintillators 4, 34, 44 are arranged in a one-dimensional manner.

Although the present embodiment showed an example of the apparatus using three radiation image detectors 3, the number of radiation image detectors 1 is not limited to this, but may be increased or decreased with necessity. Hereinafter, the apparatus 5 is called as an elongated radiation image detecting module.

The apparatus 5 is so arranged that the length of the ray entrance surface can be selected depending upon a measured object or a measurement range, whereby the measurement can be done along a very long length.

Figure 4A:
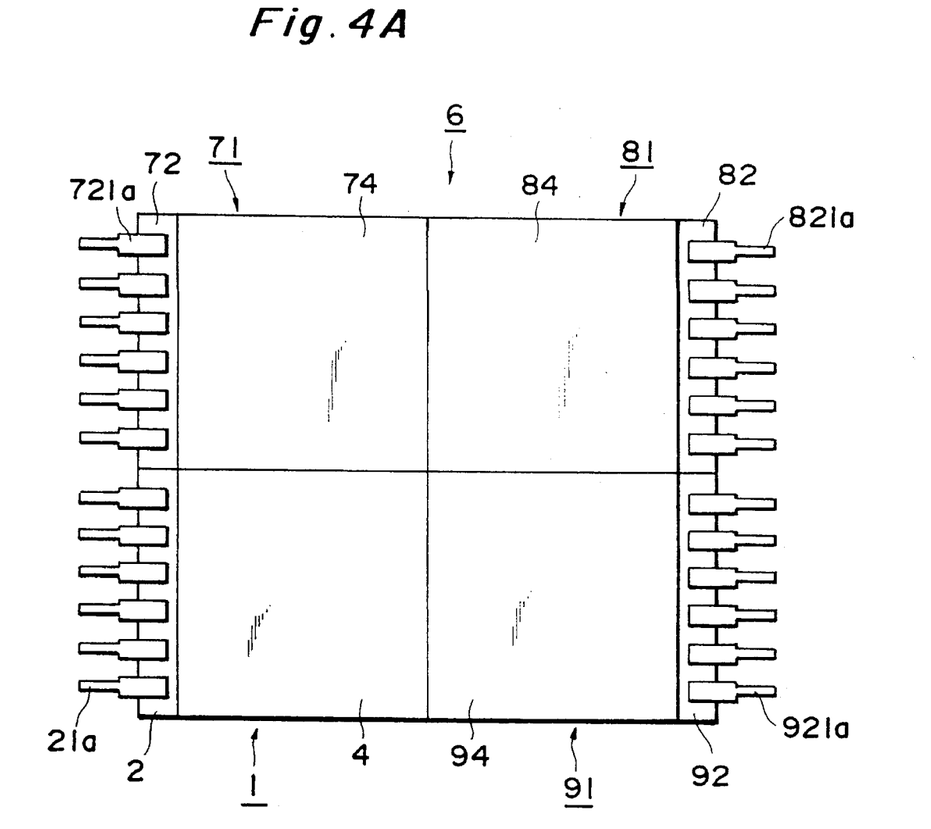
FIG. 4A is a plan view to show a radiation detecting module of an embodiment.
Figure 4B:
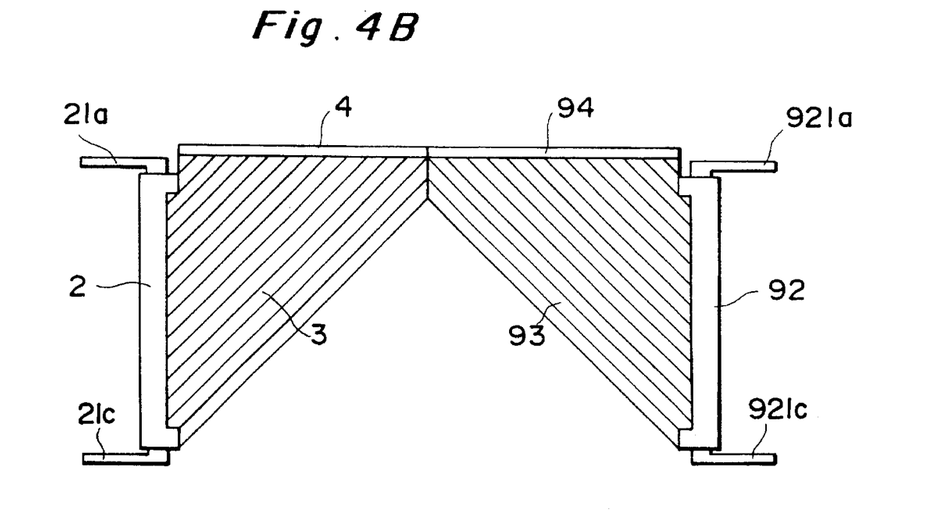
FIG. 4B is a front elevation to show the radiation detecting module of the embodiment.

FIG. 4A is a plan view of an apparatus 6 for detecting radiations. FIG. 4B is a front elevation of the apparatus 6.

As shown in FIG. 4A and FIG. 4B, this radiation image detection module 6 is provided with the radiation detector 1. The apparatus 6 is further provided with radiation detectors 71, 81, 91. The apparatus 6 thus uses four radiation detectors. Scintillators 4, 74, 84, 94 are arranged on a same plane. The scintillators 4, 74, 84, 94 are formed in a two-dimensional arrangement.

FIG. 4A shows four radiation image detectors 1. However, the number of radiation image detectors 1 is not limited to this, but may be increased or decreased with necessity.

The apparatus 6 of FIG. 4A is so arranged that the length or width of the ray entrance surface can be selected depending upon a measured object or a measured range, whereby the measurement of radiation can be done in a very wide range.

Figure 5:
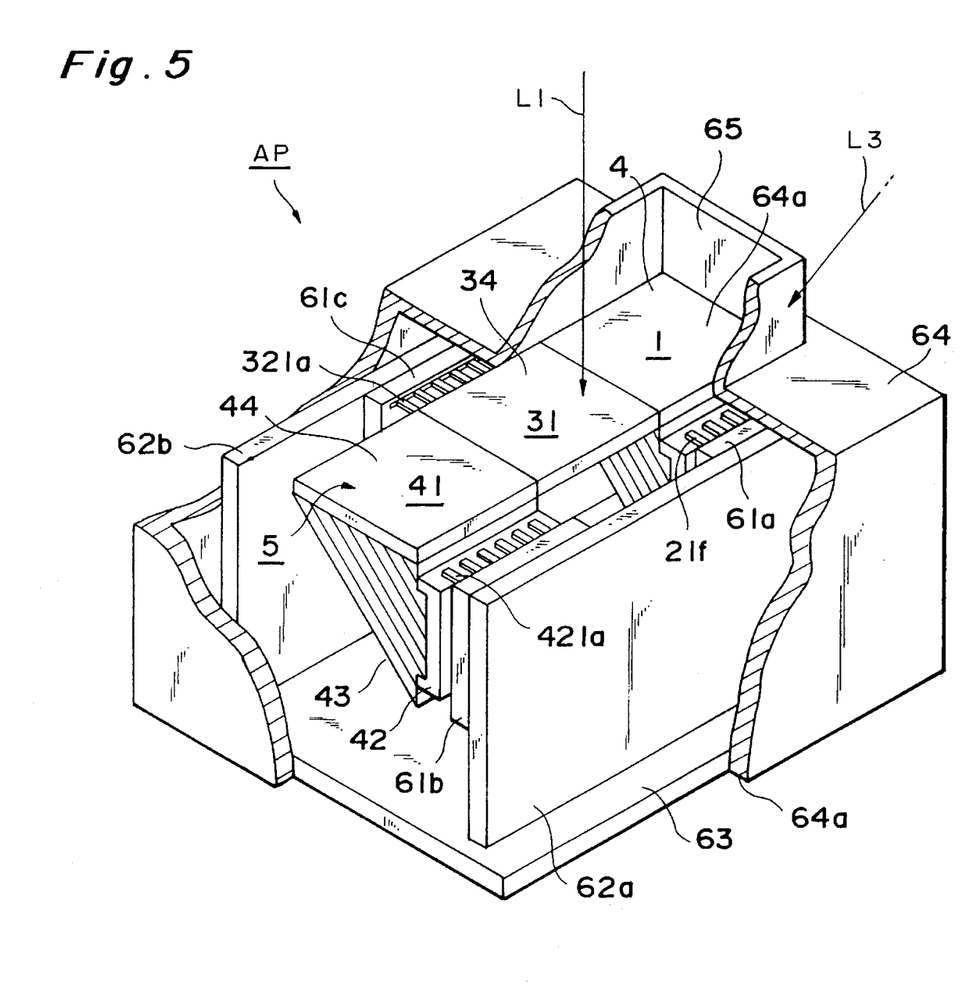
FIG. 5 is a perspective view to show a radiation image detecting apparatus of an embodiment.

As shown in FIG. 5, a radiation image detecting apparatus AP has the elongated radiation image detection module 5, three CCD sockets 61a, 61c, 61b connected to terminals 21f, 321a, 421a, respectively, of CCDs in the respective radiation image detectors 1, 31, 41 constituting the elongated radiation image detection module 5, a CCD drive circuit board 62a to which two CCD sockets 61a, 61b out of the CCD sockets 61a, 61c, 61b are attached, and a CCD drive circuit board 62b opposed to the CCD drive circuit board 62a and provided with the CCD socket 61c. The CCD drive circuit board 62a and CCD drive circuit board 62b are fixed to a bottom plate 63. Further, a radiation shielding member 64 of a box shape, made of a material which can shield the radiations such as lead, is fixed to the bottom plate 63. This radiation shielding member 64 has an opening 64a in the bottom thereof. The shielding member 64 has a rectangular window 64a at a predetermined portion on the top surface thereof so that the scintillators 4, 34, 44 are exposed to the outside. A radiation shielding barrel 65, formed of a material which can shield the radiation, such as lead, is provided around the rectangular window 64a, whereby radiation L3 is prevented from being incident in an oblique direction. The radiation L3 coming in an oblique direction is also prevented from entering the ray entrance surface of CCD 2.

As described above, according to the radiation detector 1 of the present embodiment, the scintillator is provided on the ray input face of the optical fiber plate having the ray output face and ray input face nearly perpendicular to each other and each intersecting with the waveguide direction of light, and the solid state image sensing device on the ray output face, thereby enabling a compact apparatus on the whole to be formed.

Therefore, the radiation image detector can be obtained with less dead space, in a compact size, and without temporal deviation between incidence of radiation into the scintillator and arrival of light at the CCD.

Since the surface of scintillator which the light enters is perpendicular to the ray input face of CCD, the radiation having passed through the scintillator does not enter the ray input face of CCD. Therefore, a damage of CCD due to the radiation can be prevented and the noise due to the radiation can be reduced, thus improving the S/N ratio.

As described above in detail, according to the radiation image detector of the present invention, the length of the optical fiber plate in the radiation entrance direction can be shortened, thereby obtaining the compact radiation image detector. Also, the radiation having passed through the scintillator can be perfectly prevented from entering the ray input face of the solid state image sensing device, whereby the damage of the solid state image sensing device and the noise can be reduced.

Figure 6:
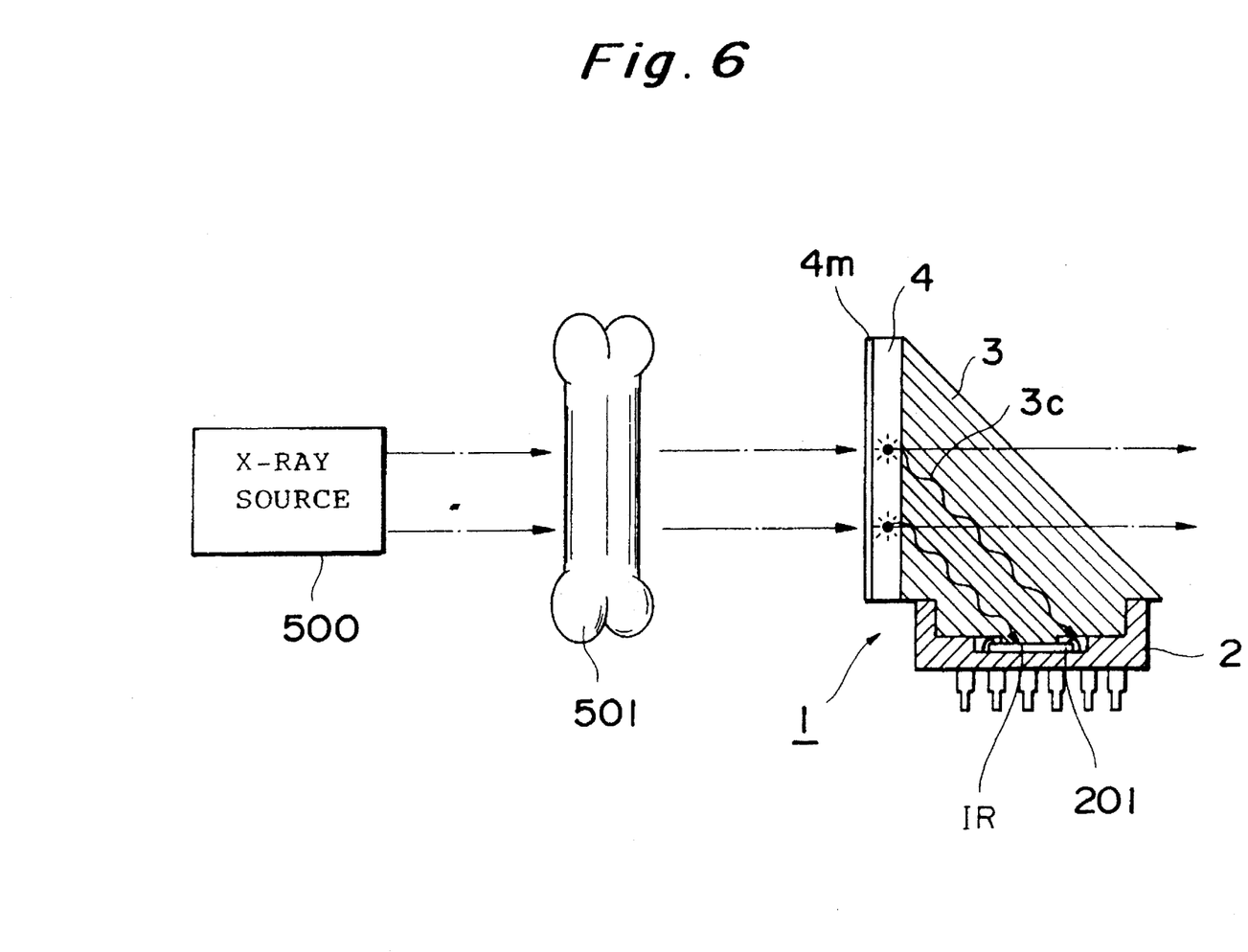
FIG. 6 is an apparatus of an embodiment.

FIG. 6 shows an embodiment of apparatus for inspecting an object (bone or teeth) made of calcium with radiation. The present apparatus is provided with a radiation source 500 and the module 1 shown in FIG. 1. Radiations (X-rays) emitted from the radiation source 500 are projected onto the object 501 including calcium, as set between the radiation source 500 and the module 1. The X-rays impinge on the luminescent screen 4.

The X-rays pass through the fiber optic device 3.

With irradiation of X-rays on the luminescent screen 4 luminescence is generated in the luminescent screen. A metal film (metal back) 4m of aluminum is stuck onto the luminescent screen. The luminescence generated in the luminescent screen 4 is reflected by the metal film 4m to advance from the metal film 4m in a direction toward the fiber optic device 3. Accordingly, the generated luminescence propagates in the cores in the fiber optic device 3 to impinge on an image pickup region IR in a CCD chip 201 of CCD image sensor 2.

The apparatus described above is further explained using FIG. 7 and FIGS. 8A–8C.

Figure 7:
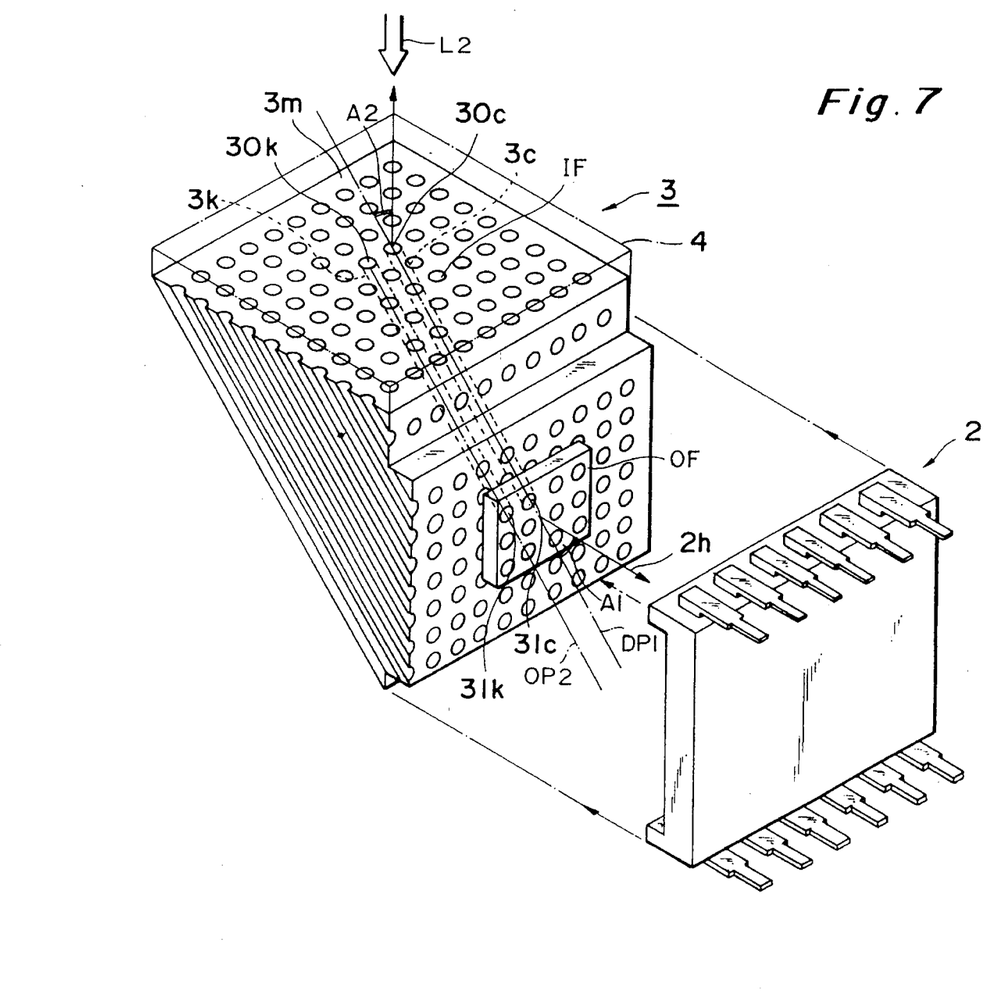
FIG. 7 is a perspective view of a fiber optic device and a CCD image sensor of an embodiment.

The fiber optic device 3 includes a plurality of optical fibers fixed to each other. Since the optical fibers are fixed to each other, the fiber optic device 3 is free of deformation. The optical fibers comprise a cladding 3m, and cores 3c, 3k buried in the cladding 3m. A refractive index of cores 3c is higher than that of the cladding 3m. The cores 3c and cladding 3m are made of glass. In the fiber optic device 3, the plurality of cores 3c, 3k, are buried in the single cladding 3m.

The fiber optic device 3 has an input face IF where the light generated in the luminescent screen 4 with entrance of radiation L2 thereinto is incident, and an output face OF where the light is outgoing. The input face IF and output face OF include end faces 30c, 30k of the cores 3c, 3k of optical fibers. The light entering the input face IF propagates in the cores 3c, 3k of optical fibers then to leave the output face OF.

The luminescent screen (luminescent film) 4 is fixed to the input face IF. The luminescent screen 4 converts a radiation ray L2 incident thereinto into a luminescent ray.

Materials for the luminescent screen 4 are described in U.S. Pat. No. 5,079,423.

The luminescence generated in the luminescent screen propagates in the core 3c, 3k to be outgoing from the output face OF of the fiber optic device 3.

The CCD image sensor 2 is fixed to the output face OF.

The CCD image sensor 2 has a package 200, and a CCD chip 201 mounted in the package 200. The package 200 has a recessed portion 200a. The fiber optic device 3 has a projected portion 3f. The projected portion 3f of the fiber optic device 3 includes the output face OF. The projected portion 3f of the fiber optic device 3 fits in with the recessed portion 200a of package 200 of the CCD image sensor 2. Accordingly, the fiber optic device 3 is stuck to the CCD image sensor 2, so that they are stationary to each other.

The CCD chip 201 has a main surface MF. The main surface MF has an image pickup region comprised of a plurality of pixels PX, and an output region OR in which bonding pads BP for collecting signals obtained from these pixels PX are formed. The image pickup region IR is a surface to which the luminescence generated in the luminescent screen 4 is incident. The image pickup region IR of CCD chip 201 is opposed to the output face OF of fiber optic device 3.

An angle A1 between the optical axis OP1, OP2 of core 3c, 3k of the fiber optic device 3 and the normal line 2h to the output face OF is 45 degrees. The image pickup region IR of CCD chip 201 is parallel to the output face OF of fiber optic device 3.

An angle A2 between the optical axis OP1 of core 3c and the normal line to the input face IF is 45 degrees. The luminescent screen 4 is parallel to the input face IF.

The output face OF includes the end faces 31c, 31k of the plurality of cores 3c, 3k. The input face IF includes the end faces 30c, 30k of the plurality of cores 3c, 3k. A density per unit area (/cm²) of the end faces 31c, 31k of the plurality of cores 3c, 3k in the output face OF is equal to a density per unit area (/cm²) of the end faces 30c, 30k of the cores 3c, 3k in the input face IF. These densities are within the range of $2.5 \times 10^6/cm^2$ to $1.0 \times 10^7/cm^2$.

Each core 3c, 3k extends straight. The optical axis OP1, OP2 of each core 3c, 3k is a straight line. Accordingly, a ray image entering the input face IF of fiber optic device 3 is output at 1:1 magnification from the output face OF. Also, an image output from the output face OF is free from distortion.

The image pickup region IR of CCD chip 201 is in contact with the output face IR of fiber optic device 3. Accordingly, an image incident to the image pickup region IR is never disturbed by any intervening members between them, whereby a clear image is incident to the image pickup region IR.

In the present detecting apparatus, the image pickup region IR of CCD chip 201 is in direct contact with the output face OF of fiber optic device 3 in order to obtain a clear image. The output region OR in which the bonding pads BP of CCD chip 201 are formed restricts this "direct contact." The output region OR is not in contact with the output face OF. Since the output face OF is not in direct contact with the output region OR, the bonding pads BP, and bonding wires 203 connecting between the bonding pads BP and lead pins 21a are prevented from being damaged by the fiber optic device 3. The bonding wires 203 stand long use.

Figure 8A:
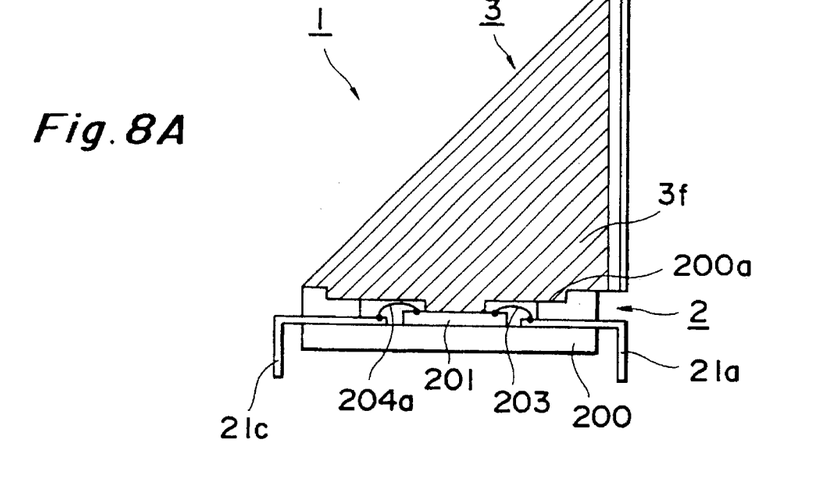
FIG. 8A to FIG. 8C are drawings to show a detecting apparatus of an embodiment.
Figure 8B:
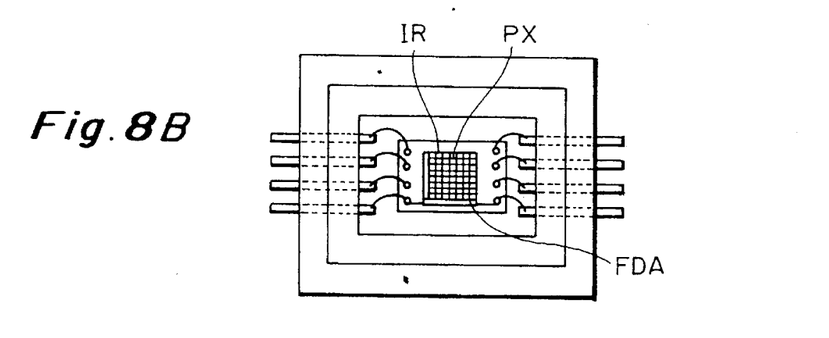
Figure 8C:
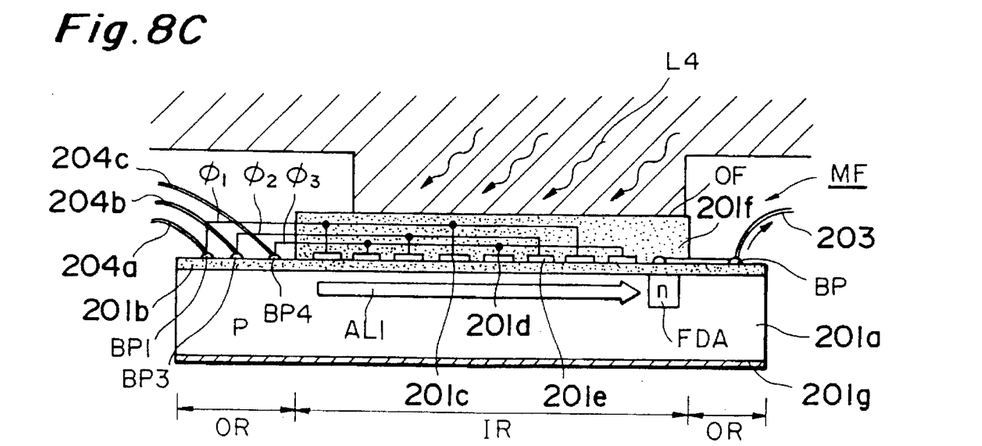

The CCD chip 201 comprises a semiconductor substrate 201a, an insulating film (silicon dioxide) 201b on and in contact with the semiconductor substrate 201a, transfer electrodes 201c, 201d, 201e in contact with the insulating film 201b, a protective layer (Phospho-Silicate Glass, PSG) 201f formed over the transfer electrodes 201c, 201d, 201e, a first signal line Φ1 for applying a predetermined drive voltage to the transfer electrodes 201c, a first bonding pad BP1 connected to the first signal line Φ1, a floating diffusion amplifier FDA for collecting signals (charge) transferred from the transfer electrodes 201c, 201d, 201e, and a second bonding pad BP connected to the floating diffusion amplifier FDA. The output region OR is a region where the first and second bonding pads BP1, BP are formed.

When a ray L4 generated in the luminescent screen 4 is incident into the p-type silicon substrate 201a, an electron-hole pair is generated in the semiconductor substrate 201a. When a potential higher than a potential of back contact 201g is given to the signal lines Φ1 to Φ3, that is, when a positive voltage is applied to the signal lines Φ1 to Φ3, electrons are attracted toward the transfer electrodes 201c, 201d, 201e. While the positive voltage is applied to the signal lines Φ1 to Φ3, generated electrons are accumulated near the interface between the oxide film 201b and the semiconductor substrate 201a. When a three-phase drive voltage is applied through the signal lines Φ1 to Φ3 to the transfer electrodes 201c, 201d, 201e, the accumulated electrons are transferred in the direction of arrow AL1 in FIG.

8C. The transferred electrons are collected by a diode formed by the n-type semiconductor region FDA to flow through the bonding pad BP and signal line 203 to the lead pin 21a. The signal lines Φ1 to Φ3 are connected to the bonding pads BP1 to BP3, respectively. A drive voltage is supplied through the bonding wire 204a, 204b, or 204c to the bonding pad BP1, BP2, or BP3, respectively. The bonding wires 204a, 204b, 204c are connected to the lead pins 21b, 21c, 21d, respectively.

The present detecting apparatus is provided with a second module 801 shown in FIG. 9. The second module 801 has the same structure as the first module 1, having a second fiber optic device 803, a second luminescent screen 804, and a second CCD image sensor 802.

The first luminescent screen 4 and second luminescent screen 804 are formed on a same plane. The normal line to the first luminescent screen (luminescent surface) 4 and the normal line to the second luminescent screen 804 are parallel to each other. The normal line to the first luminescent screen (luminescent surface) 4 and the normal line to the luminescent screen 804 are approximately parallel to each other. An angle between these normal lines is smaller than 5 degrees. A second metal film 804m is fixed to the luminescent screen 804.

The first module 1 and second module 804 are set in a housing 64. The housing 64 has a radiation shielding member. The radiation shielding member is made of lead. The housing 64 has a barrel portion 65. The barrel portion 65 has an opening 65a. A radiation L2 to be detected enters the luminescent screen 4 through the opening 65a. The barrel portion 65 is made of lead. Lead does not transmit the radiation. Since this detecting apparatus has the barrel portion 65, the directivity of radiation L2 incident into the luminescent film 4 can be enhanced. The barrel portion 65 has an opening edge 65b, an internal surface 65c intersecting with the opening edge 65b, and an external surface 65d intersecting with the opening edge 65b. The barrel portion 65 interrupts the radiation L3 obliquely incident relative to the direction of axis AX of the barrel portion 65 of the detecting apparatus from the outside of housing 64.

The first CCD image sensor 2 of the first module 1 is fixed to a first circuit board 61a for processing signals output from the CCD image sensor 2. The second image sensor 802 is fixed to a second circuit board 861a for processing signals output from this CCD image sensor 802.

The first circuit board 61a comprises a first print board 69a, and a processing circuit 69b formed on the first print board. The second circuit board 861a comprises a second print board 869a, and a processing circuit 869b formed on the second print board 869a. The first print board 69a and second print board 869a are opposed to each other. The first print board 69a and second print board 869a are nearly parallel to each other. An angle between normal lines to the first print board 69a and to the second print board 869a is less than 5 degrees. The first print board 69a and second print board 869a are fixed to the housing 64.

Image signals from the CCD chips 201, 8201 are put into a display 901 through a display controller 900 to be indicated on the display 901.

Figure 10:
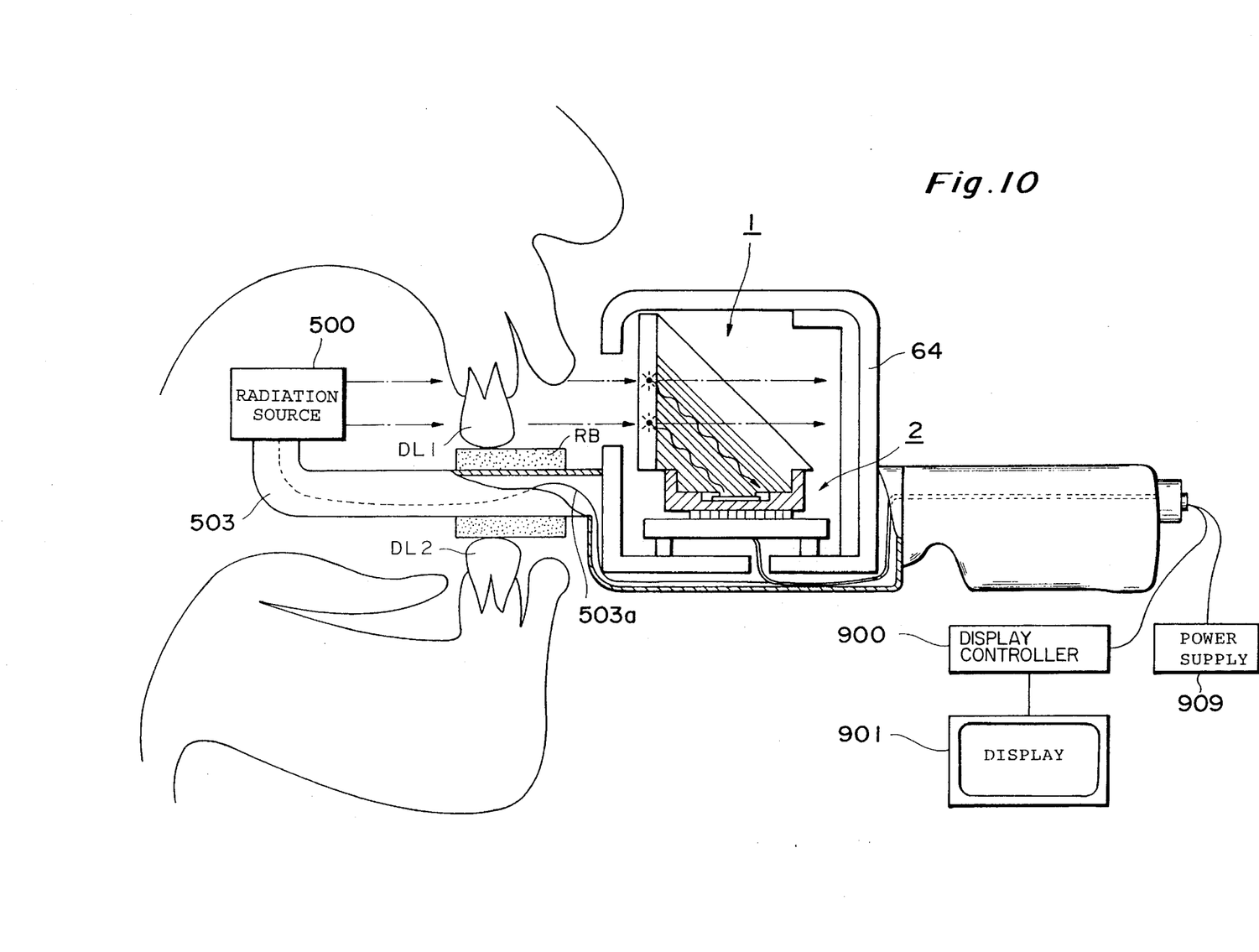
FIG. 10 is a drawing to show a detecting apparatus.

FIG. 10 shows an apparatus for detecting an image of teeth. This apparatus has a radiation source 500 connected to the housing 64. A hollow connection member 503 connects the housing 64 with the radiation source 500. Inside the connection member 503 wiring 503a is set through for supplying drive power to the radiation source (X-ray generating apparatus). Rubber RB is wound around the connection member 503. When teeth DL1, DL2 are in contact with the rubber RB, the radiation source 500 is held by the teeth.

This detecting apparatus is provided with a display 901 for indicating signals output from the CCD image sensor 2. The display 901 and CCD image sensor 2 are connected to each other through a display controller 900. The display controller 900 controls the display 901 to indicate the signals output from the CCD image sensor 2 on the display 901. The display controller 900, the liquid crystal display 901 and radiation source 500 are electrically connected to a power supply 902, and are driven by the electricity from the power supply 902.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for detecting a ray, comprising a first module:

wherein said first module comprises:

a first fiber optic device having a plurality of cores buried in a cladding, each of said plurality of cores having a first end face and a second end face, said first fiber optic device comprising an input face which includes said first end faces and to which a ray is incident and an output face which includes said second end faces and from which a ray is outgoing;

a first luminescent screen fixed to said input face; and a first CCD image sensor fixed to said output face, said CCD image sensor comprising a package, a CCD chip fixed in said package, lead pins penetrating said package, and bonding wires connecting said lead pins to said CCD chip, wherein said CCD chip comprises an image pickup region for converting a ray incident thereto into an electric signal, and bonding pads in contact with said bonding wires and wherein said output face is in contact with said image pickup region and said output face is not in contact with said bonding pads, and wherein said package has a recessed portion, said fiber optic device has a projected portion, and said projected portion of said fiber optic device fits in with the recessed portion of said package.

2. An apparatus according to claim 1, wherein said CCD chip comprises a semiconductor substrate, an insulating layer in contact with said semiconductor substrate, transfer electrodes in contact with said insulating layer, and a protective film formed over said transfer electrodes, and wherein said protective layer is in contact with said output face.

3. An apparatus according to claim 2, wherein said CCD chip further comprises signal lines connecting said transfer electrodes with said bonding pads, and wherein with application of a drive voltage to said bonding pads a potential of said transfer electrodes is changed and with incidence of rays electrons accumulated in said semiconductor substrate are transferred.

4. An apparatus according to claim 3, wherein said CCD chip further comprises a floating diffusion amplifier for collecting said electrons.

5. An apparatus according to claim 1, wherein an angle between an optical axis of one of said cores and a normal line to said output face is 45 degrees and an angle between the optical axis of said one of said cores and a normal line to said input face is 45 degrees.

6. An apparatus according to claim 1, wherein a density per unit area of said first end faces in the input face is equal to a density per unit area of said second end faces in the output face.

7. An apparatus according to claim 1, comprising a second module, wherein said second module having:
   a second fiber optic device,
   a second luminescent screen mounted to said second fiber optic device, and
   a second CCD image sensor mounted to said second fiber optic device,
   wherein said first luminescent screen and second luminescent screen are formed on a same plane.

8. An apparatus according to claim 7, wherein an angle between a normal line to said first luminescent screen and a normal line to the second luminescent screen is smaller than 5 degrees.

9. An apparatus according to claim 7, comprising:
   a housing for housing said first module;
   a first circuit board fixed to said first CCD image sensor, for processing a signal output from said first CCD image sensor; and
   a second circuit board fixed to said second CCD image sensor, for processing a signal output from said second CCD image sensor;
   wherein said first and second circuit boards are fixed to said housing and are opposed to each other.

10. An apparatus according to claim 1, further comprising a housing for housing said first module.

11. An apparatus according to claim 10, wherein said housing is comprised of a material for shielding a radiation.

12. An apparatus according to claim 10, wherein said housing is made of lead.

13. An apparatus according to claim 10, wherein said housing has a barrel portion having an opening, and a ray to be detected is incident through said opening into said first luminescent screen.

14. An apparatus according to claim 10, wherein said housing has a barrel portion having an opening, said barrel portion shielding a radiation, and a ray to be detected is incident through said opening into said first luminescent screen.

15. An apparatus according to claim 14, wherein said barrel portion has an opening edge, an inner surface intersecting with said opening edge, and an outer surface intersecting with said opening edge, and said barrel portion interrupts a radiation obliquely incident thereto relative to a direction of an axis of said barrel portion.

16. An apparatus for detecting a ray, comprising:
   a first module,
   a housing for housing said first module,
   a radiation source connected to the housing,
   a hollow connection member for connection between said housing and said radiation source,
   a wiring passing inside said connection member, for supplying drive power to the radiation source, and
   a rubber member wound around the connection member,
   wherein said first module comprises:
   a first fiber optic device having a plurality of cores buried in a cladding, each of said plurality of cores having a first end face and a second end face, said first fiber optic device comprising an input face which includes said first end faces and to which a ray is incident and an output face which includes said second end faces and from which a ray is outgoing;
   a first luminescent screen fixed to said input face; and
   a first CCD image sensor fixed to said output face, said CCD image sensor comprising a package, a CCD chip fixed in said package, lead pins penetrating said package, and bonding wires connecting said lead pins to said CCD chip,
   wherein said CCD chip comprises an image pickup region for converting a ray incident thereto into an electric signal, and bonding pads in contact with said bonding wires and wherein said output face is in contact with said image pickup region and said output face is not in contact with said bonding pads, and
   wherein when said rubber member is in contact with teeth, said radiation source is held by the teeth.

17. An apparatus for detecting a ray, comprising:
   a CCD image sensor comprising a package and a CCD chip housed in said package;
   a fiber optic device consisting of a cladding and a plurality of cores buried in said cladding, said fiber optic device contacting said CCD chip and sealing said package; and
   a first luminescent screen fixed to said fiber optic device.

* * * * *